(12) United States Patent
Betz

(10) Patent No.: US 6,864,794 B2
(45) Date of Patent: Mar. 8, 2005

(54) METHOD AND APPARATUS FOR EVALUATING MEDICAL EXAMINATION IMAGES

(75) Inventor: Roland Betz, Vjereth-Trunstadt (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 10/096,296

(22) Filed: Mar. 12, 2002

(65) Prior Publication Data
US 2002/0144697 A1 Oct. 10, 2002

(30) Foreign Application Priority Data
Mar. 14, 2001 (DE) .......................... 101 12 307

(51) Int. Cl.⁷ .......................................... G08B 23/00
(52) U.S. Cl. .................. 340/573.1; 340/506; 340/517; 340/522; 340/525; 340/825.06; 340/825.19

(58) Field of Search ............................. 340/573.1, 506, 340/517, 522, 525, 825.06, 825.19; 600/300, 407; 128/922

(56) References Cited

U.S. PATENT DOCUMENTS

| | | | |
|---|---|---|---|
| 5,235,510 A | * 8/1993 | Yamada et al. | 364/413.02 |
| 5,359,513 A | * 10/1994 | Kano et al. | 364/413.23 |
| 5,386,508 A | * 1/1995 | Itonori et al. | 395/161 |
| 5,917,929 A | * 6/1999 | Marshall et al. | 382/128 |

* cited by examiner

Primary Examiner—Hung Nguyen
(74) Attorney, Agent, or Firm—Schiff Hardin LLP

(57) ABSTRACT

In a method and to an apparatus for evaluating a sequence of medical examination images successively presented at a viewing device using a data processing device operating on software having an evaluation algorithm for determining image regions exhibiting abnormalities, an acoustic signal is emitted by the dependent on the determination result, and/or the presentation time of an image on a monitor is influenced dependent thereon.

22 Claims, 1 Drawing Sheet

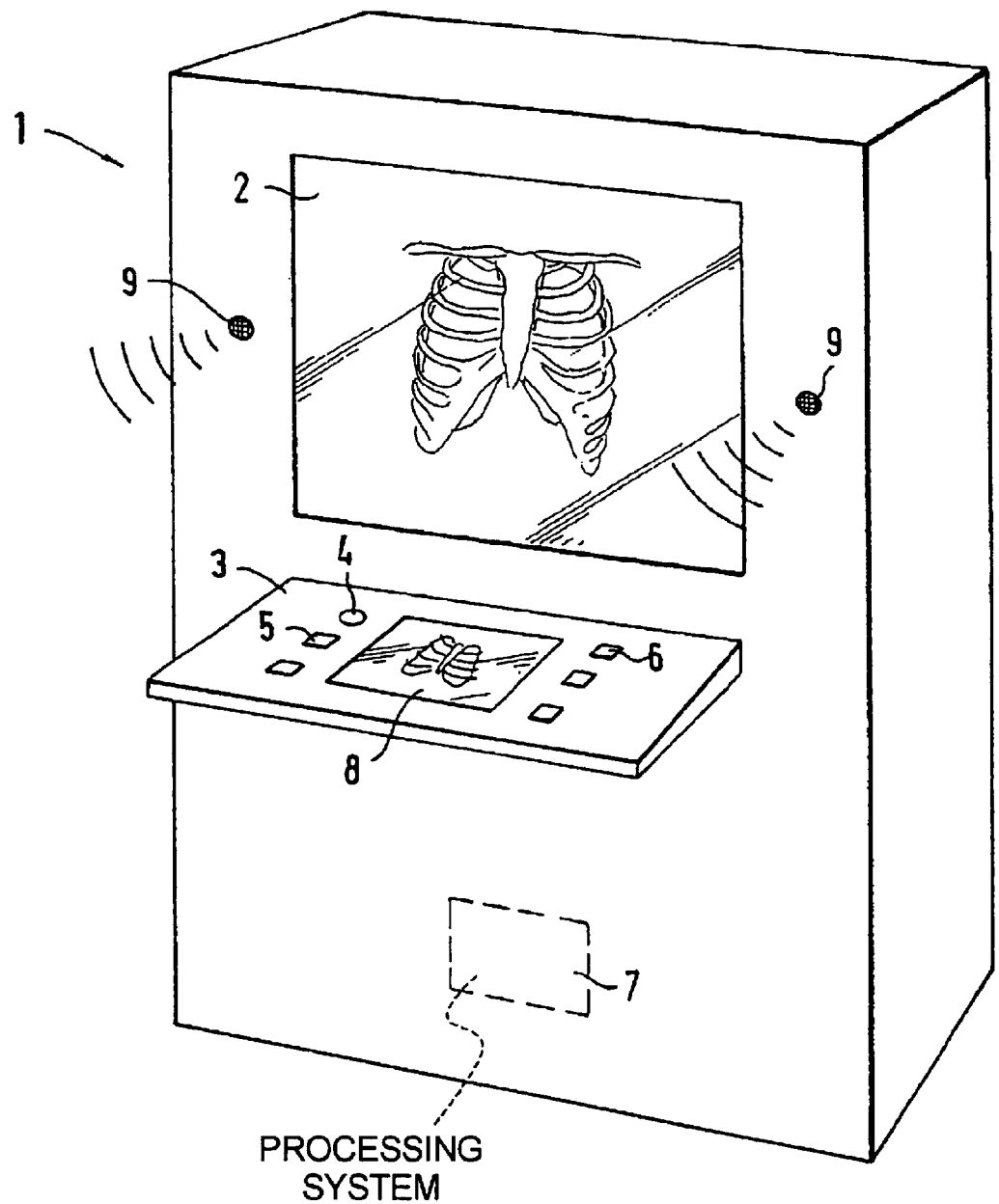

METHOD AND APPARATUS FOR EVALUATING MEDICAL EXAMINATION IMAGES

BACKGROUND OF THE INVENTION

1. Field of the Invention

The present invention is directed to a method and an apparatus for evaluating a sequence of medical examination images successively presented at a viewing device by means of a data processing device running on software having an evaluation algorithm for determining image regions exhibiting abnormalities.

2. Description of the Prior Art

Technical progress in medical technology has lead to a great increase of examination results in image form. There is a tendency to implement series examinations at a large number of patients, with a few images, for example, four examination images, being respectively for each patient. This is the case implemented, for example, in mammography and in lung examinations for detecting tuberculosis. By contrast, there are examination methods wherein tens of thousands of examination images from a single patient arise. Examples of this are tomography, MR, angiography and spiral CT. In all of these examination methods, an extremely high amount of data arises in the form of images that must be subsequently analyzed in order to determine pathological changes or abnormalities.

In particular, examination images of series examinations can be interpreted by machine in the meantime. To that end, the examination image, for example an x-ray film, is digitalized and analyzed in a data processing device running on software. The software program determines regions having characteristic structures in the digital image data and compares these to known patterns in order to recognize peculiarities or changes of an organ or of a tissue. Specific clinical pictures are distinguished by characteristic geometrical phenomena; for example, breast cancer can be recognized in an early stage on the basis of calcium agglomerations, referred to as micro-calcifications. After the discovery of a suspicious image region, this can be optically marked on a picture screen, for example by dot markings or the center of several points by a geometrical figure. This method, however, is not 100% reliable, so that all images must be monitored by a physician. Due to the large number of images, it can easily occur that images having abnormalities are overlooked, since the individual images are viewed for only a very brief time. Since the individual images differ only in terms of their details, fatigue often occurs after some time during this procedure, so that images having abnormalities can be overlooked. There is therefore the risk that examination images having symptoms of diseases are not recognized.

SUMMARY OF THE INVENTION

An object of the present invention is to provide a medical image evaluation method and apparatus which avoid the aforementioned disadvantages and enhance the dependability in the evaluation of examination images.

This object is achieved in accordance with the invention in a method of the type initially described wherein an acoustic signal is emitted dependent on the determination result and/or the presentation time of an image is influenced dependent thereon.

In addition to the visual information, the viewer is provided with an acoustic signal that draws the attention of the viewer to abnormalities or unusual deviations. The audio signal may only be emitted given images having abnormalities. Alternatively, a constant basic sound can be emitted that is modified in pitch given an image having abnormalities.

In the inventive method, additionally or alternatively the presentation time of the image can be influenced given an image having abnormalities. It therefore possible to lengthen the display time for those images wherein the software has recognized abnormalities. On the basis of the result of the evaluation algorithm, a pre-selection is undertaken in the inventive method for those images that need more detailed evaluation. As a result, the viewer can concentrate his or her attention on the images exhibiting abnormalities and is relieved of viewing and checking an extremely large number of images without deviations.

In an embodiment of the inventive method no acoustic signal, or a pleasant acoustic signal, is emitted given an image without abnormalities and/or the presentation time is shortened. The pleasant acoustic signal can be a fundamental acoustic tone. Given images without abnormalities, the presentation time is shortened, i.e. the individual images are successively shown at a higher speed. Despite the machine pre-evaluation, an exact monitoring is required since some deviations are not detected by the software program.

In order to take the extent of the abnormalities into consideration, it can be provided that a high and/or loud acoustic signal can be emitted given an image having slight abnormalities and/or the presentation time is lengthened. Given an image having many abnormalities, an acoustic alarm signal can be emitted and/or the image sequence can be stopped. By varying the variation of the volume and the pitch, two further parameters are obtained for influencing the acoustic signal. Especially high dependability is achieved when both features are simultaneously realized, i.e. when both an alarm signal is emitted and the continuous image presentation is interrupted given an image having many abnormalities.

In a further embodiment of the inventive method the abnormalities have probabilities allocated to them by the evaluation algorithm and a threshold for the probabilities is prescribed and/or can be entered, abnormalities being optically presented on the viewing device when this threshold is upwardly transgressed and/or an acoustic signal is then emitted. For specific symptoms, the software cannot unambiguously decide whether an abnormality is present. Dependent on the intensity of the abnormality, however, probabilities for the individual image regions can be assigned, those images being marked therewith that require a more detailed viewing. On the basis of the preselected threshold for the probabilities, those images can be eliminated when it is certain that no basic optical checking by a physician is required. Accordingly, the acoustic signal is also emitted only when the threshold is upwardly transgressed.

An apparatus for the implementation of the inventive method is also a subject matter of the invention. The inventive apparatus for presenting and evaluating medical examination images has a data processing device, operating on a software having an evaluation algorithm for determining image regions exhibiting abnormalities and a signal emitter drivable dependent on the determination result for generating an acoustic signal. Additionally or alternatively, an arrangement for influencing the presentation time of an image can also be provided.

The signal emitted for generating the acoustic signal can be a speaker. The inventive apparatus can also include an input unit for user pre-setting of the pitch and/or the volume and/or the timbre of the acoustic signal. The apparatus also can include an input unit for entering a threshold for the abnormalities, the signal emitter for generating the acoustic signal being driven and/or the image sequence being stopped given upward transgression thereof.

DESCRIPTION OF THE DRAWINGS

The FIGURE shows an apparatus for the presentation and evaluation of medical examination images constructed and operating in accordance with the principles of the present invention

DESCRIPTION OF THE PREFERRED EMBODIMENTS

Medical examination images, for example x-ray images, can be presented at a viewing device 2 of the apparatus 1. A greater number of such images can be placed into the apparatus 1 and can be automatically sequentially presented. Each image is presented for a specific, relatively short time in order to be viewed by the physician. After the time has elapsed, the next image is automatically presented. Various presentation parameters can be set at a control panel 3 via a rotary knob 4 and input keys 5. Further input keys 6 are arranged at the control panel 3 that enable a marking of images with peculiarities in order to subsequently study these x-ray images exactly. The x-ray images are digitalized in the apparatus, i.e. are converted into computer-readable image data. To that end, the apparatus 1 contains a data processing device 7 (shown with broken lines) which is a high-performance computer. The data processing device 7 has software available with an evaluation algorithm for detecting peculiarities in individual image regions. The digitized images can be presented at a monitor 8 that is integrated into the control panel 3. The viewer sees the original x-ray image on the viewing device 2 as well as the digitized image on the monitor 8. In the image presentation on the monitor 8, the viewer is provided with an optical assistance by image regions having abnormalities being identified by a geometrical symbol. When, for example, tissue changes have been found by the evaluation algorithm, this regions is marked on the monitor 8. Individual points can, for example, be identified with circles or triangles.

The apparatus 1 further has speakers 9 that are arranged at both sides of the viewing device 2. During the sequential presentation of the images on the viewing device 2, a continuous tone having a constant volume and frequency is emitted by the speaker 9. The pitch, the volume and a threshold can be set by the rotary knob 4 and the input keys 5—the pitch or the volume or the playback speed being modified when this threshold is upwardly transgressed. Likewise, the timbre of the acoustic signal can be modified. When the evaluation algorithm of the software program of the data processing system 7 finds an abnormality, an alarm tone is emitted instead of the pleasant continuous tone. This alarm signal can be a high tone; alternatively it can be a combination of two or more tones that are simultaneously emitted and have an unpleasant effect on the viewer of the image. Additionally, the presentation time of an x-ray image on the viewing device 2 is influenced. Images without a finding or without abnormalities are sequentially shown with a constant presentation time. When the software program has found an abnormality, the presentation time is lengthened. Given significant abnormalities, the image remains still on the viewing device 2 and/or monitor 8.

Although modifications and changes may be suggested by those skilled in the art, it is in the intention of the inventor to embody within the patent warranted hereon all changes and modifications as reasonably and properly come within the scope of his contribution to the art.

I claim as my invention:

1. A method for evaluating a sequence of medical examination images comprising the steps of:
   successively presenting medical examination images in a sequence at a viewing device;
   controlling presentation of said medical examination images at said viewing device with a data processing device running on software, including control of a presentation duration at said viewing device of each of said medical examination images;
   using said software in said data processing device, executing an evaluation algorithm for identifying if a medical examination image in said sequence exhibits an abnormality; and
   upon identification of said abnormality, said software automatically lengthening said presentation duration of the medical examination image containing the abnormality.

2. A method as claimed in claim 1 wherein said viewing device is capable of emitting an acoustic signal, and comprising the additional step of, when no abnormality is identified, emitting no acoustic signal.

3. A method as claimed in claim 2 comprising emitting a high-pitched acoustic signal upon identification of said abnormality.

4. A method as claimed in claim 2 comprising emitting a loud acoustic signal upon identification of said abnormality.

5. A method as claimed in claim 2 wherein said evaluation algorithm identifies a medical examination image containing more than one abnormality, and comprising emitting an acoustic alarm signal upon identification of more than one abnormality in a medical examination image.

6. A method as claimed in claim 1 wherein said viewing device is capable of emitting an acoustic signal, and comprising continuously emitting a pleasant acoustic signal as long as no abnormality is identified.

7. A method as claimed in claim 6 comprising emitting a high-pitched acoustic signal upon identification of said abnormality.

8. A method as claimed in claim 6 comprising emitting a loud acoustic signal upon identification of said abnormality.

9. A method as claimed in claim 1 wherein said evaluation algorithm identifies a medical examination image containing more than one abnormality, and comprising stopping successive presentation of said sequence of medical images at said viewing device upon identification of more than one abnormality in a medical examination image so that the medical examination image wherein more than one abnormality was identified remains presented at said viewing device.

10. A method as claimed in claim 1 comprising, in said evaluation algorithm, allocating respective probabilities to abnormalities which are identified, comparing said abnormalities which are identified to a probability threshold, and optically presenting said abnormality on said viewing device if said probability threshold is exceeded.

11. A method as claimed in claim 1 comprising, in said evaluation algorithm, allocating respective probabilities to abnormalities which are identified, comparing said abnormalities which are identified to a probability threshold, and initiating said response only if said probability threshold is exceeded.

12. An apparatus for evaluating a sequence of medical examination images, comprising:

a viewing device at which medical examination images are successively present in a sequence;

a data processor, running on software, controlling presentation of said medical examination images at said viewing device, including controlling a presentation duration at said viewing device of each of said medical examination images;

said software in said data processor executing an evaluation algorithm for identifying if a medical examination image in said sequence exhibits an abnormality; and upon identification of said abnormality, said data processor automatically lengthening said presentation duration of the medical examination image containing the abnormality.

13. An apparatus for evaluating a sequence of medical examination images as claimed in claim 12 comprising an acoustic emitter capable of emitting an acoustic signal, and wherein said data processor, as long as no abnormality is identified, causes no acoustic signal to be emitted.

14. An apparatus for evaluating a sequence of medical examination images as claimed in claim 13 wherein said data processor causes said signal emitter to emit a high-pitched acoustic signal upon identification of said abnormality.

15. An apparatus for evaluating a sequence of medical examination images as claimed in claim 13 wherein said data processor causes said signal emitter to emit to a loud acoustic signal upon identification of said abnormality.

16. An apparatus for evaluating a sequence of medical examination images as claimed in claim 12 comprising an acoustic emitter capable of emitting an acoustic signal, and wherein said data processor causes said signal emitter to continuously emit a pleasant acoustic signal as long as no abnormality is identified.

17. An apparatus for evaluating a sequence of medical examination images as claimed in claim 16 wherein said data processor causes said signal emitter to emit a high-pitched acoustic signal upon identification of said abnormality.

18. An apparatus for evaluating a sequence of medical examination images as claimed in claim 16 wherein said data processor causes said signal emitter to emit to a loud acoustic signal upon identification of said abnormality.

19. An apparatus for evaluating a sequence of medical examination images as claimed in claim 12 comprising an acoustic emitter capable of emitting an acoustic signal, and wherein said evaluation algorithm identifies medical examination image containing more than one abnormality, and wherein said data processor causes said signal emitter to emit an acoustic alarm signal upon identification of more than one abnormality in a medical examination image.

20. An apparatus for evaluating a sequence of medical examination images as claimed in claim 12 wherein said data processor stops successive presentation of said sequence of medical images at said viewing device upon identification of more than one abnormality in a medical image so that the medical examination image wherein more than one abnormality was identified remains presented at said viewing device.

21. An apparatus for evaluating a sequence of medical examination images as claimed in claim 12 wherein said evaluation algorithm allocates respective probabilities to abnormalities which are identified, compares said abnormalities which are identified to a probability threshold, and causes said data processor to optically present said abnormality on said viewing device if said probability threshold is exceeded.

22. An apparatus for evaluating a sequence of medical examination images as claimed in claim 12 wherein said evaluation algorithm allocates respective probabilities to abnormalities which are identified, compares said abnormalities which are identified to a probability threshold, and causes said data processor to initiate said response only if said probability threshold is exceeded.

* * * * *